United States Patent [19]

Günther et al.

[11] 4,197,401
[45] Apr. 8, 1980

[54] STILBENES, PROCESS FOR THE MANUFACTURE THEREOF AND THE USE THEREOF AS OPTICAL BRIGHTENERS

[75] Inventors: Dieter Günther, Kelkheim; Rüdiger Erckel, Hofheim am Taunus; Günter Rösch, Bad Soden am Taunus, all of Fed. Rep. of Germany

[73] Assignee: Hoechst Aktiengesellschaft, Frankfurt am Main, Fed. Rep. of Germany

[21] Appl. No.: 890,597

[22] Filed: Mar. 20, 1978

[30] Foreign Application Priority Data

Mar. 24, 1977 [DE] Fed. Rep. of Germany ....... 2712942

[51] Int. Cl.² .......................................... C07D 471/04
[52] U.S. Cl. ................................ 542/434; 252/301.22; 252/301.24; 542/464
[58] Field of Search ................... 252/301.24, 301.28; 542/434, 464; 260/307 D

[56] References Cited

U.S. PATENT DOCUMENTS

| | | | |
|---|---|---|---|
| 3,058,989 | 10/1962 | Buell et al. | 542/464 X |
| 3,412,089 | 11/1968 | Ohkawa | 252/301.24 X |
| 3,712,888 | 1/1973 | Kaempfen | 542/434 X |
| 3,926,969 | 12/1975 | Fleck et al. | 260/307 D X |
| 3,928,228 | 12/1975 | Crounse | 542/434 X |
| 3,974,172 | 8/1976 | Sahm et al. | 260/307 D |

*Primary Examiner*—Arthur P. Demers
*Attorney, Agent, or Firm*—Connolly and Hutz

[57] ABSTRACT

Compounds of the formula I

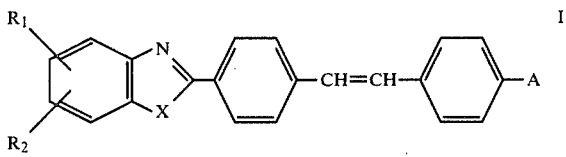

in which X is O or S, $R_1$ and $R_2$, being identical or different, are radicals selected from the group of hydrogen, fluorine or chlorine atoms, phenyl, $C_1$–$C_9$-alkyl, $C_1$–$C_4$-alkoxy, $C_1$–$C_4$-dialkyl-amino, acylamino radicals, or optionally functionally modified carboxy or sulfo groups, two adjacent radicals $R_1$ and $R_2$ together optionally representing a benzo ring, a lower alkylene or a 1,3-dioxapropylene group, and A is a group of the formulae

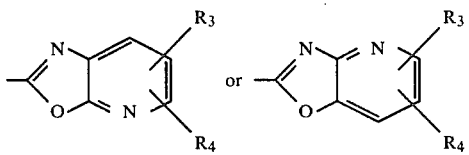

in which $R_3$ and $R_4$, independently from each other, are hydrogen, fluorine or chlorine atoms or $C_1$–$C_4$-alkyl groups.

3 Claims, No Drawings

STILBENES, PROCESS FOR THE MANUFACTURE THEREOF AND THE USE THEREOF AS OPTICAL BRIGHTENERS

Subject of the present invention are compounds of the formula I

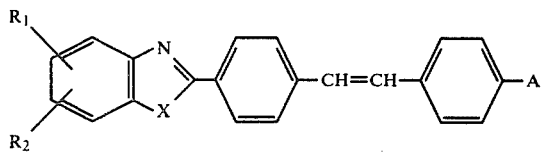

in which X is O or S, $R_1$ and $R_2$, being identical or different, are radicals selected from the group of hydrogen, fluorine or chlorine atoms, phenyl, $C_1$–$C_9$-alkyl, $C_1$–$C_4$-alkoxy, $C_1$–$C_4$-dialkylamino, acylamino radicals, or optionally functionally modified carboxy or sulfo groups, two adjacent radicals $R_1$ and $R_2$ together optionally representing a benzo ring, a lower alkylene or a 1,3-dioxapropylene group, and A is a group of the formulae

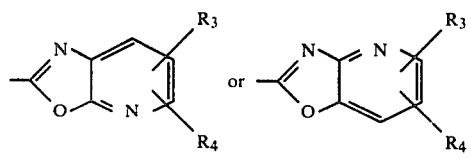

in which $R_3$ and $R_4$, independently from each other, are hydrogen, fluorine or chlorine atoms or $C_1$–$C_4$ alkyl groups.

Especially interesting are those compounds of the formula I, in which X, $R_1$ and $R_2$ are as defined above and $R_3$ and $R_4$, independently from each other, are hydrogen or methyl.

Preferred compounds are above all those of the formula I, in which X is O, $R_1$ and $R_2$, independently from each other, are hydrogen or chlorine atom in 5-, 6- or 7-position, $C_1$–$C_4$-alkyl, phenyl or, together, are a fused benzo ring, and $R_3$ and $R_4$, independently from each other, are hydrogen.

By functionally modified carboxy groups, there are to be understood generally carboxylic acid derivatives in every respect, that is, compounds having one carbon atom which is linked to three hetero atoms, especially oxygen, nitrogen and sulfur. In a more limited sense, there are to be understood salts with colorless cations, alkali metal or ammonium ions being preferred, and furthermore a cyano, carboxylic acid ester or carboxylic acid amide group. By carboxylic acid ester groups, there are to be understood especially those of the formula $COOQ^1$, in which $Q^1$ is a phenyl radical or an optionally branched lower alkyl group. By carboxylic acid amide group, there is to be understood especially a group of the formula $CONQ^2Q^3$, in which $Q^2$ and $Q^3$ are hydrogen atoms or optionally substituted lower alkyl groups which may form a hydroaromatic ring together with the nitrogen atom.

By functionally modified sulfo groups, there are to be understood, in analogy to the above details, radicals the sulfo group of which is linked to a hereto atom, that is, salts with colorless cations, preferably alkali metal or ammonium ions, and furthermore sulfonic acid ester groups and the sulfonamide group. By sulfonic acid ester group, there is to be understood especially a group of the formula $SO_2OQ^1$, in which $Q^1$ is as defined above, and by sulfonamide group, there is to be understood a group of the formula $SO_2NQ^2Q^3$, in which $Q^2$ and $Q^3$ are as defined above.

By acyl group, there is to be understood especially a group of the formula $COQ^4$, in which $Q^4$ is an optionally substituted, preferably lower, alkyl radical, or a phenyl radical, especially an unsubstituted $C_1$–$C_4$-alkanoyl group or the benzoyl group.

The novel compounds of the formula I can be prepared according to different methods already known.

According to one of these manufacturing processes, compounds of the formula II

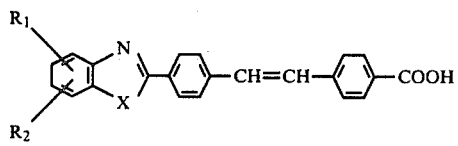

are reacted, with or without intermediate isolation, and preferably in the presence of catalysts, with compounds of the formula III

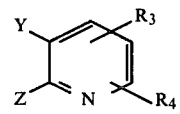

in which either z is an amino group and Y a hydroxy group or Y is an amino group and Z a hydroxy group or a chlorine atom. Instead of the free acids of the formula II, the functional derivatives thereof may alternatively be used as starting materials, for example the corresponding alkyl ester or, preferably, the acid chloride. In the above formulae, the symbols X, $R_1$, $R_2$, $R_3$ and $R_4$ are as defined sub formula I.

The reaction of the components may be carried out with or without intermediate isolation, by heating to elevated temperatures, for example to 120° to 330° C., advantageously in an inert gas, for example a nitrogen current, and the reaction is optionally carried out in the presence of a catalyst. Suitable catalysts are for example boric acid, zinc chloride, p-toluenesulfonic acid, furthermore polyphosphoric acids including pyrophosphoric acid. When using boric acid as catalyst, it is employed advantageously in an amount of from about 0.5 to 5%, relative to the total weight of the reaction mass. High-boiling, polar, organic solvents such as dimethyl formamide, N-methylpyrrolidone, and aliphatic, optionally etherified, oxy compounds, for example dialkyl carbinols, propylene glycol, ethyleneglycol-monoethyl ether or diethyleneglycol-diethyl ether, and high-boiling esters of phthalic acid, for example phthalic acid dibutyl ester, may be used in addition.

Alternatively, this reaction may be carried out in two steps by condensing the carboxylic acid of the formula II or a functional derivative thereof, especially a carboxylic acid chloride, with a compound of the formula III in the presence of an organic solvent such as toluene, xylylene, chlorobenzene, dichlorobenzene, tetraline, trichlorobenzene or nitrobenzene, at elevated temperatures, and converting the N-acyl compounds so obtained to the compounds of formula I at elevated temperatures and optionally in the presence of a catalyst.

This operation mode is required especially in the case where Z in the formula III is a chlorine atom. In this case, cyclization of the acyl compound obtained in the first step to a compound of formula I has to be carried out according to known processes, as described for example in British Pat. No. 1,242,836 or U.S. Pat. No. 3,873,531, in the presence of copper acetate and metallic zinc.

When carboxylic acid chlorides are used as starting substances of the formula II, they may be prepared immediately prior to condensation with the compounds of formula III and without intermediate isolation with thionyl chloride from the free carboxylic acid in the same solvent in which subsequently the condensation with the compound III proceeds.

When Z in the formula III is an amino group and Y a hydroxy group, compounds of the formula I are obtained having an oxazolo-(4,5-b)-pyridine ring, while in the inverse case compounds of the formula I having an oxazolo-(5,4-b)-pyridine ring are the result.

The free acids of the formula II and the corresponding acid chlorides are known from the literature and can be obtained according to processes described in the literature (Japanese Pat. Nos. 40,581/65, 44–6979, 7045/68, German Offenlegungsschriften Nos. 2,306,050, 1,594,829, 2,129,816). They are obtained for example by the following reaction steps known to those skilled in the art:

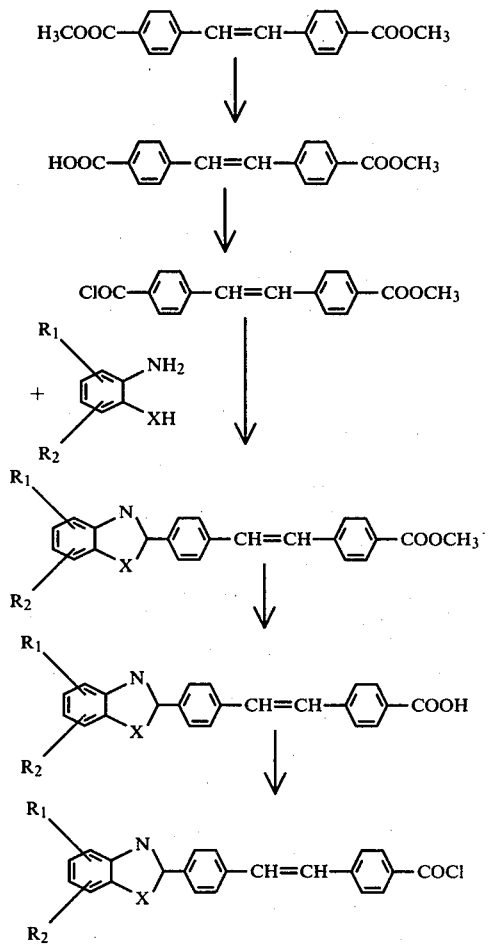

The compounds of the formula III are known from the literature and can be obtained according to processes described in the literature (German Offenlegungsschrift No. 2,628,266, French Pat. Nos. 1,477,998, 1,522,261, British Patent No. 1,108,975, J.Chem.Soc.B 1971 (7) 1425–32).

The novel compounds of the formula I are nearly colorless to yellow fluorescing substances which are suitable as optical brighteners and above all as blending component in admixture with other optical brighteners.

The substrates to be brightened are for example the following materials: lacquers, natural or synthetic fibers, for example those of natural or regenerated cellulose, acetyl cellulose, natural or synthetic polyamides, such as wool, polyamide-6 and polyamide-6,6, polyesters, polyolefins, polyvinyl chloride, polyvinylidene chloride, polystyrene or polyacrylonitrile, furthermore sheets, films, ribbons or shaped articles made from these materials.

The water-insoluble compounds of the invention may be used in the form of solutions in organic solvents or in aqueous dispersions advantageously with addition of a dispersing agent.

Suitable dispersing agents are for example soaps, polyglycol ethers derived from fatty alcohols, fatty amines or alkylphenols, cellulose sulfite waste liquors or condensation products of optionally alkylated naphthalene-sulfonic acids with formaldehyde.

The compounds of the formula I may alternatively be added to detergents, which latter ones may contain the usual fillers and auxiliaries, such as alkali metal silicates, alkali metal phosphates or polymetaphosphates, alkali metal borates, alkali metal salts of carboxymethylcellulose; foam stabilizers such as alkanolamides of higher fatty acids; or complex forming agents such as soluble salts of ethylene-diamine-tetraacetic acid or diethylene-triamine-pentaacetic acid; or chemical bleaching agents such as perborates or percarbonates.

Brightening of the fiber material with the aqueous or possibly organic brightening liquor is carried out either according to the exhaust process at temperatures of from preferably 20° to 150° C., or under thermosol conditions; the textile material being adjusted to a redisual moisture content of from about 50 to about 120% by impregnation or spraying with the brightener solution or dispersion and squeezing between rollers. Subsequently, the textile material is subjected for about 10 to 300 seconds to a heat treatment, preferably by means of dry heat, at temperatures of from about 120° to about 240° C. This thermosol process may be combined with other finishing operations, for example application of synthetic resins in order to obtain easy care properties.

The compounds of the invention may furthermore be added to high molecular weight organic materials before or during their processing. They may be added for example when manufacturing films, sheets, ribbons or shaped articles from the corresponding molding compositions, or they may be dissolved in the spinning mass before the spinning operation. Suitable compounds may also be added to low molecular starting materials before the polycondensation or polymerization of, for example, polyamide-6, polyamide-6,6 or linear polyesters of the polyethyleneglycol terephthalate type.

Compounds of the invention being substituted by one or, preferably, two carboxyl or carbalkoxy groups may be linked to linear polyester molecules or synthetic polyamides via an ester or an amide, when they are added to these materials or, preferably, their starting substances under suitable conditions. Brighteners anchored in the substrate in this manner by chemical linkage are distinguished by their extraordinary fastness to sublimation and to solvents.

The amount of compounds of the formula (1) to be used in accordance with this invention, relative to the material to be optically brightened, may vary within wide limits, depending on the field of application and the intended effect, and it may be determined easily by simple preliminary tests. Generally it is from about 0.01 to about 2%.

The following Examples illustrate the invention, parts and percentages being by weight unless otherwise stated.

EXAMPLE 1

36 g (0.1 mol) of 4'-benzoxazolyl-2-stilbene-4-carboxylic acid chloride are introduced into a suspension of 10.1 g (0.1 mol) of 2-amino-3-pyridinol in 360 ml of trichlorobenzene, and the whole is stirred for 5 hours at 150°–160° C. Subsequently, 2 g of p-toluenesulfonic acid are added and the water of reaction which has formed is eliminated at reflux temperature. After having completely removed the water, the batch is cooled to 80° C., 180 ml of methanol are added, and the mixture is refluxed for a further 30 minutes. After cooling, the reaction product is suction-filtered, and washed with methanol. After drying, 37.7 g (90.7% of the theoretical yield) of the compound having the formula

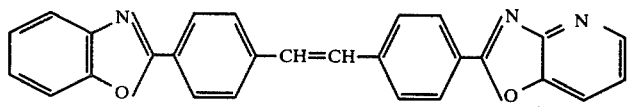

are obtained which, after recrystallization from N-methylpyrrolidone and clarification with animal charcoal, is present in the form of a light yellow powder having a melting point of 330°–333° C.

| Analysis: | calc. | found |
|---|---|---|
| C | 77.9 | 77.6 |
| H | 4.1 | 4.3 |
| N | 10.1 | 9.9 |

UV-absorption: (measured in DMF): $\tau\mathrm{max} = 378$ nm; $\epsilon = 8.62 \times 10^4$.

EXAMPLE 2

37.4 g (0.1 mol) of 4'-(5-methyl-benzoxazolyl-2-)-stilbene-4-carboxylic acid chloride are introduced into a suspension of 10.1 g (0.1 mol) of 2-amino-3-pyridinol in 360 ml of tetraline, and the whole is stirred for 6 hours at 150°–160° C. Subsequently, 2 g of $P_2O_5$ are added and the water of reaction which has formed is eliminated at reflux temperature. Splitting-off of water being complete, the batch is cooled to 80° C., 180 ml of methanol are added, and the mixture is refluxed for a further 30 minutes. After cooling, the reaction product is suction-filtered and washed with methanol. After drying, 35.2 g (82% of the theoretical yield) of a compound having the formula

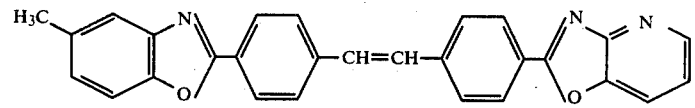

are obtained which, after recrystallization from N-methylpyrrolidone with clarification by means of animal charcoal, is present in the form of a light yellow powder having a melting point of more than 300° C.

| Analysis: | calc. | found |
|---|---|---|
| C | 78.30 | 78.1 |
| H | 4.46 | 4.5 |
| N | 9.98 | 9.8 |

UV-absorption (measured in DMF): $\tau\mathrm{max} = 378$ nm; $\epsilon = 8.58 \times 10^4$.

EXAMPLE 3

17 g (50 mmols) of 4'-benzoxazolyl-2-stilbene-4-carboxylic acid in 200 ml of toluene are converted to the acid chloride with addition of excess thionyl chloride and catalytic amounts of dimethyl formamide by refluxing for 5 hours. Subsequently, excess thionyl chloride is distilled off. After cooling, 6.5 g (50 mmols) of 3-amino-2-chloropyridine are added, and the batch is refluxed for a further 16 hours. After cooling, the product is suction-filtered, washed with methanol and dried. 17.7 g (78.4%) of the following compound

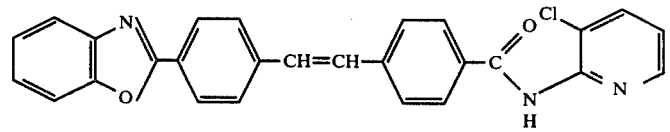

having a melting point (crude product) of 237°–238° C. are obtained.

EXAMPLE 4

4.5 g (10 mmols) of the compound obtained according to Example 3 are refluxed for 3 hours in 30 ml of dry pyridine and 90 ml of dry dimethyl formamide with addition of 5.7 g of dried copper acetate and 1.1 g of zinc granules. After cooling, the batch is poured into 1 liter of water, suction-filtered, and the residue is precipitated by agitation first with 2 N aqueous ammonia, subsequently with 2% potassium carbonate solution, washed to neutral with water and dried. 4.1 g (98% of the theoretical yield) of the following compound

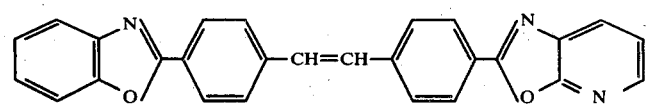

are obtained which, after recrystallization from N-methylpyrrolidone, have the form of light yellow crystals having a melting point of 340°–342° C.

| Analysis: | calc. | found |
|---|---|---|
| C | 78.0 | 77.9 |
| H | 4.1 | 4.0 |
| N | 10.1 | 10.3 |

(UV-absorption (measured in DMF): $\tau$max=374 nm; $\epsilon$=87900.

EXAMPLE 5

When 4'-(5-phenyl-benzoxazol-2)-stilbene-4-carboxylic acid chloride is used for the batch of Example 3, and operations are carried out according to Examples 3 and 4, the following compound

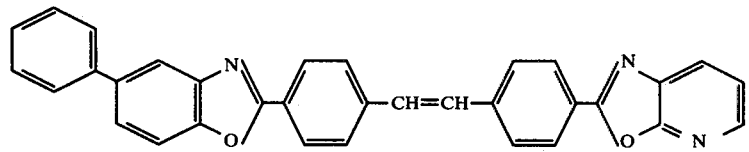

is obtained with a 52% yield relative to the carboxylic acid chloride used, which after recrystallization from N-methylpyrrolidone with clarification by means of animal charcoal has the form of light yellow crystals having a melting point of 300°–305° C.
UV-absorption (measured in DMF): $\tau$max=378 nm; $\epsilon$=85700.

EXAMPLE 6

According to the operations of Example 1, the following compound

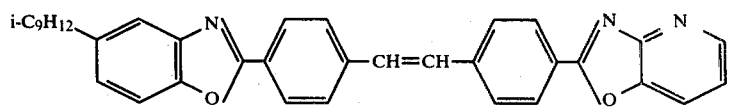

is obtained which, after recrystallization from N-methylpyrrolidone with purification by means of animal charcoal has the form of light yellow crystals having a melting point of 284°–286° C.

| Analysis: | calc. | found |
|---|---|---|
| C | 79.85 | 78.9 |
| N | 6.47 | 6.3 |
| H | 7.76 | 7.4 |

UV-absorption (measured in DMF): $\tau$max=378 nm; $\epsilon$=80100.

According to Examples 3 and 4, the following compounds are obtained:

EXAMPLE 7

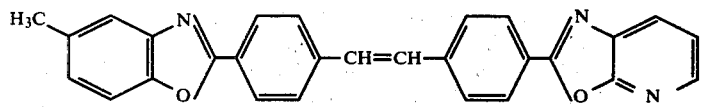

melting point 318°–320° C.

| Analysis: | calc. | found |
|---|---|---|
| C | 78.2 | 78.1 |
| H | 4.4 | 4.5 |
| N | 9.8 | 9.8 |

UV-absorption (measured in DMF): $\tau$max=377 nm; $\epsilon$=86800.

EXAMPLE 8

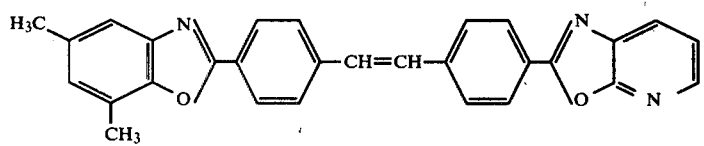

melting point 291°–294° C.

| Analysis: | calc. | found |
|---|---|---|
| C | 78.5 | 78.2 |
| H | 4.8 | 4.8 |

-continued

| Analysis: | calc. | found |
|---|---|---|
| N | 9.5 | 9.3 |

UV-absorption (measured in DMF): τmax=378 nm; ε=85700.

EXAMPLE 9

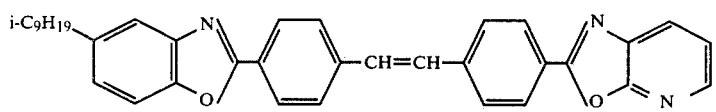

UV-absorption (measured in DMF): τmax=378 nm; ε=71100.

What is claimed is:

1. Compounds of the formula I

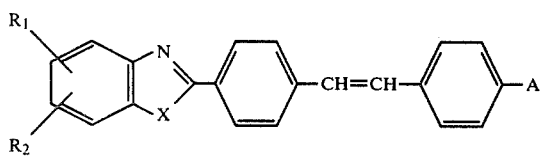

in which X is O or S, $R_1$ and $R_2$, being identical or different, are radicals selected from the group of hydrogen, fluorine or chlorine atoms, phenyl, $C_1$–$C_9$-alkyl, $C_1$–$C_4$-alkoxy, $C_1$–$C_4$-dialkylamino, acylamino radicals, or optionally functionally modified carboxy or sulfo groups, two adjacent radicals $R_1$ and $R_2$ together optionally representing a benzo ring, a lower alkylene or a 1,3-dioxapropylene group, and A is a group of the formulae

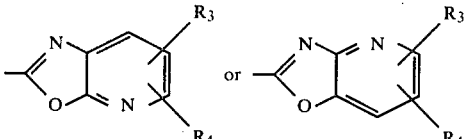

in which $R_3$ and $R_4$, independently from each other, are hydrogen, fluorine or chlorine atoms or $C_1$–$C_4$ alkyl groups.

2. Compounds as claimed in claim 1, wherein X, $R_1$ and $R_2$ are as defined in claim 1 and $R_3$ and $R_4$, independently from each other, are hydrogen or methyl.

3. Compounds as claimed in claim 1, wherein X is an oxygen atom, $R_1$ and $R_2$, independently from each other, are hydrogen or chlorine atoms in 5-, 6- or 7-position, $C_1$–$C_4$-alkyl, phenyl or, together are fused benzo ring, and $R_3$ and $R_4$, independently from each other, are hydrogen.

* * * * *